US012616617B2

(12) United States Patent
Andrews et al.

(10) Patent No.: US 12,616,617 B2
(45) Date of Patent: May 5, 2026

(54) APPARATUS AND METHOD OF MANUFACTURING AN ELASTIC COMPOSITE STRUCTURE FOR AN ABSORBENT SANITARY PRODUCT

(71) Applicant: Curt G. Joa, Inc., Sheboygan Falls, WI (US)

(72) Inventors: Robert Earl Andrews, Sheboygan, WI (US); David Edward Schuette, Kiel, WI (US); Jeffrey Wayne Fritz, Plymouth, WI (US); Justin Marshall Lafferty, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 1622 days.

(21) Appl. No.: 16/717,186

(22) Filed: Dec. 17, 2019

(65) Prior Publication Data

US 2020/0206040 A1 Jul. 2, 2020

Related U.S. Application Data

(60) Provisional application No. 62/786,609, filed on Dec. 31, 2018.

(51) Int. Cl.
*A61F 13/49* (2006.01)
*A61F 13/15* (2006.01)
(Continued)

(52) U.S. Cl.
CPC .... *A61F 13/4902* (2013.01); *A61F 13/15593* (2013.01); *A61F 13/15756* (2013.01);
(Continued)

(58) Field of Classification Search
CPC ............ A61F 13/4902; A61F 13/15593; A61F 13/15756; A61F 13/474; A61F 2013/49025; B65H 51/015; D02G 3/32
See application file for complete search history.

(56) References Cited

U.S. PATENT DOCUMENTS

| | | | |
|---|---|---|---|
| 3,580,783 A | 5/1971 | Glaze | |
| 3,589,100 A | 6/1971 | Konars et al. | |

(Continued)

FOREIGN PATENT DOCUMENTS

| | | |
|---|---|---|
| CN | 101868210 B | 9/2014 |
| EP | 0274752 A2 | 7/1988 |

(Continued)

OTHER PUBLICATIONS

Service Thread, "Thread and Yarn Tension Control—4 Benefits of Using a Creel", Service Thread, Feb. 9, 2018, https://www.servicethread.com/blog/4-benefits-of-using-a-yarn-creel-in-industrial-applications. (Year: 2018).*

(Continued)

*Primary Examiner* — Christopher W Raimund
(74) *Attorney, Agent, or Firm* — Klintworth & Rozenblat LLP

(57) ABSTRACT

An apparatus and method for manufacturing an elastic composite structure for an absorbent sanitary product includes at least one structure that guides web layers in a machine direction, an elastic thread combiner that combines a plurality of elastic threads to form a combined elastic thread assembly, and a bonding unit. The bonding unit bonds the web layers together via a bond pattern that includes bond lines that each have at least one pair of adjacent bonds, which anchor the combined elastic thread assembly within a passage defined by a pair of adjacent bonds in each of the plurality of bond lines. The passage is narrower than the combined elastic thread assembly in a non-tensioned state and wider than one of the plurality of elastic threads in a non-tensioned state.

7 Claims, 8 Drawing Sheets

(51) Int. Cl.

| | |
|---|---|
| *A61F 13/474* | (2006.01) |
| *B65H 51/015* | (2006.01) |
| *D02G 3/32* | (2006.01) |

(52) U.S. Cl.
CPC ......... *A61F 13/474* (2013.01); *B65H 51/015* (2013.01); *A61F 2013/49025* (2013.01); *D02G 3/32* (2013.01)

(56) References Cited

U.S. PATENT DOCUMENTS

| | | | |
|---|---|---|---|
| 3,622,434 A | 11/1971 | Newman | |
| 3,658,064 A | 4/1972 | Pociluyko | |
| 3,668,054 A | 6/1972 | Stumpf | |
| 3,844,869 A | 10/1974 | Rust | |
| 3,884,227 A | 5/1975 | Lutz et al. | |
| 3,982,988 A | 9/1976 | Heimberger | |
| 3,993,532 A | 11/1976 | McDonald et al. | |
| 4,088,731 A | 5/1978 | Groome | |
| 4,305,988 A | 12/1981 | Kocher | |
| 4,305,998 A | 12/1981 | Manty et al. | |
| 4,333,978 A | 6/1982 | Kocher | |
| 4,336,203 A | 6/1982 | Zucker et al. | |
| 4,443,291 A | 4/1984 | Reed | |
| 4,485,819 A | 12/1984 | Igl | |
| 4,662,005 A | 5/1987 | Grier-Idris | |
| 4,770,656 A | 9/1988 | Proxmire et al. | |
| 4,808,176 A | 2/1989 | Kielpikowski | |
| 4,833,734 A | 5/1989 | Der Estephanian | |
| 4,834,738 A | 5/1989 | Kielpikowski et al. | |
| 4,834,741 A | 5/1989 | Sabee | |
| 4,842,596 A | 6/1989 | Kielpikowski et al. | |
| 4,863,542 A | 9/1989 | Oshefsky et al. | |
| 4,919,738 A | 4/1990 | Ball et al. | |
| 4,977,011 A | 12/1990 | Smith | |
| 5,094,717 A | 3/1992 | Manning et al. | |
| 5,163,932 A | 11/1992 | Nomura et al. | |
| 5,353,798 A | 10/1994 | Sieben | |
| 5,362,433 A * | 11/1994 | Toscan .................... | D01D 5/16 |
| | | | 528/80 |
| 5,468,320 A | 11/1995 | Zafiroglu | |
| 5,530,979 A | 7/1996 | Whitley | |
| 5,561,863 A | 10/1996 | Carlson, II | |
| 5,618,378 A | 4/1997 | Cahill | |
| 5,624,420 A | 4/1997 | Bridges et al. | |
| 5,643,395 A | 7/1997 | Hinton | |
| 5,643,396 A | 7/1997 | Rajala et al. | |
| 5,660,657 A | 8/1997 | Rajala et al. | |
| 5,694,925 A | 12/1997 | Reese et al. | |
| 5,699,791 A | 12/1997 | Sukiennik et al. | |
| 5,707,470 A | 1/1998 | Rajala et al. | |
| 5,711,847 A | 1/1998 | Rajala et al. | |
| 5,745,922 A | 5/1998 | Rajala et al. | |
| 5,769,993 A | 6/1998 | Baldauf | |
| 5,789,065 A | 8/1998 | Haffner et al. | |
| 5,797,895 A | 8/1998 | Widlund et al. | |
| 5,803,075 A | 9/1998 | Yavitz | |
| 5,813,398 A | 9/1998 | Baird et al. | |
| 5,817,584 A | 10/1998 | Singer et al. | |
| 5,883,026 A | 3/1999 | Reader et al. | |
| 5,934,275 A | 8/1999 | Gazzara | |
| 5,954,055 A | 9/1999 | Miyake | |
| D424,688 S | 5/2000 | Bryant et al. | |
| 6,055,982 A | 5/2000 | Brunson et al. | |
| 6,057,024 A | 5/2000 | Mleziva et al. | |
| 6,062,220 A | 5/2000 | Whitaker et al. | |
| 6,123,077 A | 9/2000 | Bostock et al. | |
| 6,125,849 A | 10/2000 | Williams et al. | |
| 6,165,298 A | 12/2000 | Samida et al. | |
| 6,173,712 B1 | 1/2001 | Brunson | |
| 6,197,404 B1 | 3/2001 | Varona | |
| 6,213,125 B1 | 4/2001 | Reese et al. | |
| 6,217,889 B1 | 4/2001 | Lorenzi et al. | |
| 6,235,137 B1 | 5/2001 | Van Eperen et al. | |
| 6,248,197 B1 * | 6/2001 | Nakanishi ................ | D01F 6/70 |
| | | | 264/210.8 |
| 6,257,235 B1 | 7/2001 | Bowen | |
| 6,279,570 B1 | 8/2001 | Mittelstadt et al. | |
| 6,291,039 B1 | 9/2001 | Combe et al. | |
| 6,295,714 B1 | 10/2001 | Roychowdhury et al. | |
| 6,332,465 B1 | 12/2001 | Xue et al. | |
| 6,340,782 B1 | 1/2002 | Kling et al. | |
| 6,354,296 B1 | 3/2002 | Baumann et al. | |
| 6,394,090 B1 | 5/2002 | Chen et al. | |
| 6,427,693 B1 | 8/2002 | Blackstock et al. | |
| 6,460,539 B1 | 10/2002 | Japuntich et al. | |
| 6,482,278 B1 | 11/2002 | McCabe et al. | |
| 6,484,722 B2 | 11/2002 | Bostock et al. | |
| 6,506,474 B2 | 1/2003 | Tsuji | |
| 6,534,694 B2 | 3/2003 | Kling et al. | |
| 6,536,434 B1 | 3/2003 | Bostock et al. | |
| 6,541,679 B2 | 4/2003 | Betrabet et al. | |
| 6,568,392 B1 | 5/2003 | Bostock et al. | |
| 6,584,976 B2 | 7/2003 | Japuntich et al. | |
| 6,604,524 B1 | 8/2003 | Curran et al. | |
| 6,613,955 B1 | 9/2003 | Lindsay et al. | |
| 6,623,837 B2 | 9/2003 | Morman et al. | |
| 6,644,314 B1 | 11/2003 | Elsberg | |
| 6,652,693 B2 | 11/2003 | Burriss et al. | |
| 6,673,980 B1 | 1/2004 | Varona et al. | |
| 6,676,062 B1 | 1/2004 | Herhaus | |
| 6,701,992 B1 | 3/2004 | Pasquale et al. | |
| 6,712,922 B2 | 3/2004 | Sorenson et al. | |
| 6,715,489 B2 | 4/2004 | Bostock et al. | |
| 6,722,366 B2 | 4/2004 | Bostock et al. | |
| 6,730,188 B2 | 5/2004 | Sanders | |
| 6,761,710 B2 | 7/2004 | D Acchioli et al. | |
| 6,780,263 B2 | 8/2004 | Delisle | |
| 6,843,872 B2 | 1/2005 | Morman | |
| 6,886,563 B2 | 5/2005 | Bostock et al. | |
| 6,889,622 B2 | 5/2005 | Marcangelo | |
| 6,914,018 B1 | 7/2005 | Uitenbroek et al. | |
| 6,928,657 B2 | 8/2005 | Bell et al. | |
| 6,953,452 B2 | 10/2005 | Popp et al. | |
| 7,008,496 B2 | 3/2006 | Morman | |
| 7,021,227 B2 | 4/2006 | Marcangelo | |
| 7,025,841 B2 | 4/2006 | Owen | |
| 7,044,131 B2 | 5/2006 | Griesbach et al. | |
| 7,069,930 B2 | 7/2006 | Bostock et al. | |
| 7,118,558 B2 | 10/2006 | Wu et al. | |
| 7,198,688 B2 | 4/2007 | Mortell et al. | |
| 7,211,531 B2 | 5/2007 | Schneider et al. | |
| 7,217,261 B2 | 5/2007 | Otsubo et al. | |
| 7,290,545 B2 | 11/2007 | Kleman et al. | |
| 7,316,840 B2 | 1/2008 | Neculescu et al. | |
| 7,361,241 B2 | 4/2008 | Barth et al. | |
| 7,378,566 B2 | 5/2008 | Soerens et al. | |
| 7,464,516 B2 | 12/2008 | Johnson | |
| 7,469,427 B2 | 12/2008 | Yang et al. | |
| 7,507,680 B2 | 3/2009 | Middlesworth et al. | |
| 7,582,348 B2 | 9/2009 | Ando et al. | |
| 7,617,787 B2 | 11/2009 | Marcangelo | |
| 7,619,167 B2 | 11/2009 | Lee et al. | |
| 7,638,014 B2 | 12/2009 | Coose et al. | |
| 7,642,398 B2 | 1/2010 | Jarpenberg et al. | |
| 7,691,138 B2 | 4/2010 | Stenzel et al. | |
| 7,708,849 B2 | 5/2010 | McCabe | |
| 7,722,734 B2 | 5/2010 | Otsubo | |
| 7,725,948 B2 | 6/2010 | Steindorf | |
| 7,799,967 B2 | 9/2010 | Ranganathan et al. | |
| 7,833,369 B2 | 11/2010 | Zhou et al. | |
| 7,845,351 B2 | 12/2010 | Mathis et al. | |
| 7,861,756 B2 | 1/2011 | Jenquin et al. | |
| 7,901,392 B2 | 3/2011 | Kline et al. | |
| 7,955,418 B2 | 6/2011 | Claussen et al. | |
| 7,981,231 B2 | 7/2011 | Schneider et al. | |
| 8,007,484 B2 | 8/2011 | Mccabe et al. | |
| 8,074,660 B2 | 12/2011 | Duffy | |
| 8,075,543 B2 | 12/2011 | Okuda | |
| 8,091,550 B2 | 1/2012 | Steindorf | |
| 8,109,916 B2 | 2/2012 | Wennerbaeck | |
| 8,142,411 B2 | 3/2012 | Kline et al. | |
| 8,146,594 B2 | 4/2012 | Bostock et al. | |

(56)        References Cited

U.S. PATENT DOCUMENTS

| 8,182,457 | B2 | 5/2012 | Olson et al. |
| 8,182,624 | B2 | 5/2012 | Handziak |
| 8,207,395 | B2 | 6/2012 | Soerens et al. |
| 8,268,444 | B2 | 9/2012 | Okaya |
| 8,282,617 | B2 | 10/2012 | Kaneda |
| 8,298,205 | B2 | 10/2012 | Norrby et al. |
| 8,308,706 | B2 | 11/2012 | Fukae |
| 8,323,257 | B2 | 12/2012 | Melik et al. |
| 8,328,820 | B2 | 12/2012 | Diamant et al. |
| 8,360,067 | B2 | 1/2013 | Duffy |
| 8,375,950 | B2 | 2/2013 | Bostock et al. |
| 8,435,223 | B2 | 5/2013 | Roe et al. |
| 8,440,043 | B1 | 5/2013 | Schneider et al. |
| 8,470,946 | B1 | 6/2013 | Carlson |
| 8,528,560 | B2 | 9/2013 | Duffy |
| 8,562,777 | B2 | 10/2013 | Drake |
| 8,585,667 | B2 | 11/2013 | Roe et al. |
| 8,622,059 | B2 | 1/2014 | Kleman |
| 8,640,704 | B2 | 2/2014 | Spoo et al. |
| 8,647,319 | B2 | 2/2014 | Een et al. |
| 8,652,114 | B2 | 2/2014 | Roe et al. |
| 8,652,115 | B2 | 2/2014 | Roe et al. |
| 8,669,409 | B2 | 3/2014 | Roe |
| 8,702,671 | B2 | 4/2014 | Tsang et al. |
| 8,740,128 | B2 | 6/2014 | Oravits et al. |
| 8,741,083 | B2 | 6/2014 | Wennerbaeck et al. |
| 8,758,786 | B2 | 6/2014 | Hassler |
| 8,771,449 | B2 | 7/2014 | Takino et al. |
| 8,784,395 | B2 | 7/2014 | Roe et al. |
| 8,784,397 | B2 | 7/2014 | Chang et al. |
| 8,808,263 | B2 | 8/2014 | Roe et al. |
| 8,881,729 | B2 | 11/2014 | Duffy |
| 8,926,579 | B2 | 1/2015 | Wang et al. |
| 8,932,273 | B2 | 1/2015 | Roe et al. |
| 8,936,586 | B2 | 1/2015 | Roe |
| 8,992,497 | B2 | 3/2015 | Roe et al. |
| 8,998,870 | B2 | 4/2015 | Roe |
| 9,011,402 | B2 | 4/2015 | Roe et al. |
| 9,011,404 | B2 | 4/2015 | Kobayashi et al. |
| 9,012,013 | B2 | 4/2015 | Duffy |
| 9,028,462 | B2 | 5/2015 | Poole et al. |
| 9,056,033 | B2 | 6/2015 | Fenske |
| 9,060,905 | B2 | 6/2015 | Wang et al. |
| 9,078,789 | B2 | 7/2015 | Wang et al. |
| 9,078,792 | B2 | 7/2015 | Ruiz |
| 9,089,456 | B2 | 7/2015 | Roe et al. |
| 9,095,478 | B2 | 8/2015 | Roe |
| 9,180,059 | B2 | 11/2015 | Roe et al. |
| 9,301,881 | B2 | 4/2016 | Ando et al. |
| 9,387,138 | B2 | 7/2016 | Roe |
| 9,539,735 | B2 | 1/2017 | Ferguson et al. |
| 9,603,395 | B2 | 3/2017 | Duffy |
| 9,603,396 | B2 | 3/2017 | Duffy |
| 9,615,612 | B2 | 4/2017 | Duffy |
| 9,770,057 | B2 | 9/2017 | Duffy |
| 9,770,058 | B2 | 9/2017 | Angadjivand et al. |
| 9,770,611 | B2 | 9/2017 | Facer et al. |
| 9,809,414 | B2 | 11/2017 | Fritz et al. |
| 9,868,002 | B2 | 1/2018 | Duffy |
| 9,913,764 | B2 | 3/2018 | Thomas et al. |
| 10,040,621 | B2 | 8/2018 | Duffy et al. |
| 10,130,833 | B2 | 11/2018 | Angadjivand et al. |
| 10,137,321 | B2 | 11/2018 | Martin |
| 10,143,246 | B2 | 12/2018 | Houde et al. |
| D837,970 | S | 1/2019 | Henderson et al. |
| 10,182,603 | B2 | 1/2019 | Duffy |
| 10,213,348 | B2 | 2/2019 | Gualtieri et al. |
| 10,227,202 | B2 | 3/2019 | Pamperin et al. |
| 10,259,165 | B2 | 4/2019 | Ehlert et al. |
| D848,678 | S | 5/2019 | Andrews |
| 10,314,346 | B2 | 6/2019 | Potnis et al. |
| 10,329,110 | B2 | 6/2019 | Dotta |
| 10,457,436 | B2 | 10/2019 | Spencer et al. |
| 10,492,547 | B2 | 12/2019 | Weber et al. |
| 10,494,221 | B2 | 12/2019 | Harris et al. |
| 10,518,996 | B2 | 12/2019 | Adami |
| 10,537,479 | B2 | 1/2020 | Schuette et al. |
| 10,596,045 | B2 | 3/2020 | Koshijima et al. |
| 10,596,047 | B2 | 3/2020 | Coenen et al. |
| 10,751,228 | B2 | 8/2020 | Kurohara et al. |
| 10,758,428 | B2 | 9/2020 | Nakamura et al. |
| 10,786,398 | B2 | 9/2020 | Koshijima et al. |
| 10,792,194 | B2 | 10/2020 | Hohm et al. |
| 10,889,066 | B2 | 1/2021 | Begrow et al. |
| 10,893,986 | B2 | 1/2021 | Manabe et al. |
| 10,973,703 | B2 | 4/2021 | Coenen et al. |
| 11,020,281 | B2 | 6/2021 | Ishikawa |
| 11,020,286 | B2 | 6/2021 | Kaufman et al. |
| 11,117,771 | B2 | 9/2021 | Hada et al. |
| 11,129,753 | B2 | 9/2021 | Schneider et al. |
| 11,141,321 | B2 | 10/2021 | Schneider et al. |
| 11,147,717 | B2 | 10/2021 | Schneider et al. |
| 11,173,072 | B2 | 11/2021 | Fritz |
| 11,191,676 | B2 | 12/2021 | Koshijima et al. |
| 11,219,555 | B2 | 1/2022 | Schneider et al. |
| 11,254,062 | B2 | 2/2022 | Ehlert et al. |
| 11,254,066 | B2 | 2/2022 | Begrow et al. |
| 11,399,989 | B2 | 8/2022 | Polidori et al. |
| 11,433,620 | B2 | 9/2022 | Ehlert et al. |
| 11,701,268 | B2 | 7/2023 | Andrews et al. |
| 2001/0025683 | A1 | 10/2001 | Burriss et al. |
| 2001/0034508 | A1 | 10/2001 | Betrabet et al. |
| 2001/0044250 | A1 | 11/2001 | Tsuji |
| 2002/0092604 | A1 | 7/2002 | McCabe et al. |
| 2002/0116027 | A1 | 8/2002 | Egan et al. |
| 2002/0117575 | A1 | 8/2002 | Gilmore et al. |
| 2002/0119288 | A1 | 8/2002 | Morman et al. |
| 2002/0157778 | A1 | 10/2002 | Sorenson et al. |
| 2003/0051803 | A1 | 3/2003 | Sanders |
| 2003/0120250 | A1 | 6/2003 | Betrabet et al. |
| 2003/0124306 | A1 | 7/2003 | Morman |
| 2003/0125706 | A1 | 7/2003 | Popp et al. |
| 2003/0125707 | A1 | 7/2003 | Popp et al. |
| 2003/0135185 | A1 | 7/2003 | Crowther |
| 2003/0144643 | A1 | 7/2003 | Jarpenberg et al. |
| 2004/0005832 | A1 | 1/2004 | Neculescu et al. |
| 2004/0059280 | A1 | 3/2004 | Makower et al. |
| 2004/0112509 | A1 | 6/2004 | Morman |
| 2004/0116885 | A1 | 6/2004 | Soerens et al. |
| 2004/0127614 | A1 | 7/2004 | Jiang et al. |
| 2004/0138635 | A1 | 7/2004 | Sorenson et al. |
| 2004/0158217 | A1 | 8/2004 | Wu et al. |
| 2004/0192140 | A1 | 9/2004 | Schneider et al. |
| 2004/0219854 | A1 | 11/2004 | Groitzsch et al. |
| 2004/0226645 | A1 | 11/2004 | Owen |
| 2004/0243085 | A1 | 12/2004 | Veith et al. |
| 2004/0261230 | A1 | 12/2004 | Neeb et al. |
| 2005/0095942 | A1 | 5/2005 | Mueller et al. |
| 2005/0101216 | A1 | 5/2005 | Middlesworth et al. |
| 2005/0131374 | A1 | 6/2005 | Otsubo et al. |
| 2005/0142331 | A1 | 6/2005 | Anderson et al. |
| 2005/0148261 | A1 | 7/2005 | Close et al. |
| 2005/0176029 | A1 | 8/2005 | Heller et al. |
| 2005/0183646 | A1 | 8/2005 | Marcangelo |
| 2005/0216058 | A1 | 9/2005 | Egan et al. |
| 2005/0228350 | A1 | 10/2005 | Ranganathan et al. |
| 2006/0009104 | A1 | 1/2006 | Schneider et al. |
| 2006/0069373 | A1 | 3/2006 | Schlinz et al. |
| 2006/0099871 | A1 | 5/2006 | Poruthoor et al. |
| 2006/0130964 | A1 | 6/2006 | McCabe |
| 2006/0135923 | A1 | 6/2006 | Boggs et al. |
| 2006/0135932 | A1 | 6/2006 | Abuto et al. |
| 2006/0138693 | A1 | 6/2006 | Tuman et al. |
| 2006/0149208 | A1 | 7/2006 | Carr |
| 2006/0180068 | A1 | 8/2006 | Marcangelo |
| 2006/0184149 | A1 | 8/2006 | Kasai et al. |
| 2006/0224137 | A1 | 10/2006 | McCabe et al. |
| 2006/0228969 | A1 | 10/2006 | Erdman |
| 2006/0238757 | A1 | 10/2006 | Silcott |
| 2006/0270302 | A1 | 11/2006 | Ando et al. |
| 2007/0000021 | A1 | 1/2007 | Yang et al. |
| 2007/0068529 | A1 | 3/2007 | Kalatoor et al. |
| 2007/0131335 | A1 | 6/2007 | Zhou et al. |
| 2007/0175477 | A1 | 8/2007 | Baggett |

(56) References Cited

U.S. PATENT DOCUMENTS

| | | |
|---|---|---|
| 2007/0218245 A1 | 9/2007 | Schneider et al. |
| 2007/0286987 A1 | 12/2007 | Anderson et al. |
| 2008/0103460 A1 | 5/2008 | Close et al. |
| 2008/0110554 A1 | 5/2008 | Otsubo |
| 2008/0169373 A1 | 7/2008 | Andrews et al. |
| 2008/0262455 A1 | 10/2008 | Soerens et al. |
| 2008/0312625 A1 | 12/2008 | Hundorf et al. |
| 2009/0134049 A1 | 5/2009 | Melik et al. |
| 2009/0163940 A1 | 6/2009 | Sliwa |
| 2009/0208703 A1 | 8/2009 | Wennerbaeck et al. |
| 2009/0242098 A1 | 10/2009 | Handziak |
| 2009/0306616 A1 | 12/2009 | Wennerbaeck |
| 2009/0326503 A1 | 12/2009 | Lakso et al. |
| 2009/0326504 A1 | 12/2009 | Kaneda |
| 2010/0015190 A1 | 1/2010 | Hassler |
| 2010/0076390 A1 | 3/2010 | Norrby et al. |
| 2010/0076394 A1 | 3/2010 | Hayase et al. |
| 2010/0087352 A1 | 4/2010 | Mason |
| 2010/0286709 A1 | 11/2010 | Diamant et al. |
| 2010/0298798 A1 | 11/2010 | Lakso et al. |
| 2010/0324513 A1 | 12/2010 | Wennerbaeck |
| 2011/0055998 A1 | 3/2011 | Tai et al. |
| 2011/0061786 A1 | 3/2011 | Mason |
| 2011/0067797 A1 | 3/2011 | Schneider et al. |
| 2011/0118689 A1 | 5/2011 | Een et al. |
| 2011/0152811 A1 | 6/2011 | Bing-Wo et al. |
| 2011/0184372 A1 | 7/2011 | Esping et al. |
| 2011/0192888 A1 | 8/2011 | Tai et al. |
| 2011/0251576 A1 | 10/2011 | Ando et al. |
| 2011/0257616 A1 | 10/2011 | Lakso et al. |
| 2012/0088103 A1 | 4/2012 | Sugiura et al. |
| 2012/0095429 A1 | 4/2012 | Kobayashi et al. |
| 2012/0123367 A1 | 5/2012 | Melik et al. |
| 2012/0123368 A1 | 5/2012 | Melik et al. |
| 2012/0123369 A1 | 5/2012 | Melik et al. |
| 2012/0123370 A1 | 5/2012 | Melik et al. |
| 2012/0123371 A1 | 5/2012 | Melik et al. |
| 2012/0123372 A1 | 5/2012 | Melik et al. |
| 2012/0123373 A1 | 5/2012 | Melik et al. |
| 2012/0175064 A1 | 7/2012 | Yamamoto |
| 2012/0228988 A1 | 9/2012 | Cutsforth |
| 2012/0321856 A1 | 12/2012 | Afshari |
| 2012/0328841 A1 | 12/2012 | Afshari |
| 2012/0328842 A1 | 12/2012 | Afshari |
| 2013/0011601 A1 | 1/2013 | Fenske |
| 2013/0012899 A1 | 1/2013 | Fenske |
| 2013/0042411 A1 | 2/2013 | Vitale |
| 2013/0048191 A1 | 2/2013 | Durrance et al. |
| 2013/0079797 A1 | 3/2013 | Diamant et al. |
| 2013/0157012 A1 | 6/2013 | Qin et al. |
| 2013/0165896 A1 | 6/2013 | Carbonari |
| 2013/0255865 A1 | 10/2013 | Brown et al. |
| 2014/0093687 A1 | 4/2014 | Humiston et al. |
| 2014/0099469 A1 | 4/2014 | Abuto et al. |
| 2014/0102650 A1 | 4/2014 | Qin et al. |
| 2014/0180126 A1 | 6/2014 | Millett et al. |
| 2015/0050462 A1 | 2/2015 | Schroer, Jr. |
| 2015/0164705 A1 | 6/2015 | Thomas et al. |
| 2016/0058624 A1 | 3/2016 | Hohm et al. |
| 2016/0228305 A1 | 8/2016 | Gualtieri et al. |
| 2016/0288407 A1 | 10/2016 | Ehlert et al. |
| 2016/0331600 A1 | 11/2016 | Polidori et al. |
| 2017/0113366 A1 | 4/2017 | Ferguson et al. |
| 2017/0281417 A1 | 10/2017 | Ishikawa |
| 2018/0027899 A1 | 2/2018 | Facer et al. |
| 2018/0042788 A1 | 2/2018 | Kurohara et al. |
| 2018/0093444 A1 | 4/2018 | Begrow et al. |
| 2018/0140473 A1 | 5/2018 | Koshijima et al. |
| 2018/0147095 A1 | 5/2018 | Koshijima et al. |
| 2018/0168880 A1 | 6/2018 | Schneider et al. |
| 2018/0169964 A1 | 6/2018 | Schneider et al. |
| 2018/0170027 A1 | 6/2018 | Schneider et al. |
| 2018/0280209 A1 | 10/2018 | Manabe et al. |
| 2019/0000162 A1 | 1/2019 | Houde |
| 2019/0021916 A1 | 1/2019 | Ishikawa |

| | | |
|---|---|---|
| 2019/0070041 A1 | 3/2019 | Schneider et al. |
| 2019/0209396 A1 | 7/2019 | Nakamura et al. |
| 2019/0224053 A1 | 7/2019 | Nakamura et al. |
| 2019/0231606 A1 | 8/2019 | Andrews et al. |
| 2019/0274895 A1 | 9/2019 | Chen et al. |
| 2019/0358093 A1 | 11/2019 | Kaufman et al. |
| 2019/0374398 A1 | 12/2019 | Coenen et al. |
| 2019/0374404 A1 | 12/2019 | Ninomiya et al. |
| 2020/0039152 A1 | 2/2020 | Ehlert et al. |
| 2020/0179180 A1 | 6/2020 | Koshijima et al. |
| 2020/0197230 A1 | 6/2020 | Ohtsubo |
| 2020/0206043 A1 | 7/2020 | Coenen et al. |
| 2020/0214901 A1 | 7/2020 | Andrews et al. |
| 2020/0268567 A1 | 8/2020 | Coenen et al. |
| 2020/0297551 A1 | 9/2020 | Andrews et al. |
| 2020/0298545 A1 | 9/2020 | Andrews et al. |
| 2020/0299883 A1 | 9/2020 | Begrow et al. |
| 2020/0360191 A1 | 11/2020 | Nakamura et al. |
| 2020/0361158 A1 | 11/2020 | Sugiura et al. |
| 2021/0000657 A1 | 1/2021 | Hohm et al. |
| 2021/0059866 A1 | 3/2021 | Fritz et al. |
| 2021/0100695 A1 | 4/2021 | Ishibashi et al. |
| 2021/0205152 A1 | 7/2021 | Polidori et al. |
| 2021/0252796 A1 | 8/2021 | Ehlert et al. |
| 2021/0267818 A1 | 9/2021 | Kaufman et al. |
| 2022/0000676 A1 | 1/2022 | Schneider et al. |
| 2022/0071809 A1 | 3/2022 | Fritz |
| 2022/0151840 A1 | 5/2022 | Mueller et al. |
| 2022/0211553 A1 | 7/2022 | Manabe |
| 2022/0218534 A1 | 7/2022 | Minami et al. |
| 2022/0250331 A1 | 8/2022 | Weiler et al. |
| 2022/0324669 A1 | 10/2022 | Follen et al. |
| 2023/0339714 A1 | 10/2023 | Roehrborn et al. |

FOREIGN PATENT DOCUMENTS

| | | |
|---|---|---|
| EP | 0330716 A2 | 9/1989 |
| EP | 0168225 B1 | 3/1991 |
| EP | 0307871 B1 | 12/1992 |
| EP | 0386324 B1 | 6/1993 |
| EP | 0685586 A2 | 12/1995 |
| EP | 0677284 B1 | 6/1999 |
| EP | 0886480 B1 | 12/2001 |
| EP | 1166721 A2 | 1/2002 |
| EP | 1035808 B1 | 3/2004 |
| EP | 1024721 B1 | 9/2004 |
| EP | 1351815 B1 | 2/2005 |
| EP | 1555000 A2 | 7/2005 |
| EP | 1388410 B1 | 10/2005 |
| EP | 1448824 B1 | 10/2005 |
| EP | 1236827 B1 | 1/2006 |
| EP | 1029521 B1 | 4/2006 |
| EP | 1138471 B1 | 6/2006 |
| EP | 1159942 B1 | 7/2006 |
| EP | 1641417 B1 | 6/2007 |
| EP | 1547558 B1 | 10/2008 |
| EP | 1290289 B1 | 12/2008 |
| EP | 1330355 B1 | 3/2009 |
| EP | 1263989 B1 | 5/2009 |
| EP | 1330222 B1 | 8/2009 |
| EP | 1458553 B1 | 9/2009 |
| EP | 2103427 A2 | 9/2009 |
| EP | 1610950 B1 | 10/2009 |
| EP | 1715994 B1 | 3/2010 |
| EP | 1520569 B1 | 7/2010 |
| EP | 1586252 B1 | 8/2010 |
| EP | 1959907 B1 | 9/2010 |
| EP | 1525345 B1 | 4/2011 |
| EP | 1882177 B1 | 6/2011 |
| EP | 1707168 B1 | 8/2011 |
| EP | 1716831 B1 | 9/2011 |
| EP | 2083100 B1 | 9/2011 |
| EP | 2207926 B1 | 9/2011 |
| EP | 2219534 B1 | 9/2011 |
| EP | 2027841 B1 | 7/2012 |
| EP | 1595017 B1 | 8/2012 |
| EP | 1891256 B1 | 8/2012 |
| EP | 2020972 B1 | 11/2012 |
| EP | 2020974 B1 | 12/2012 |

(56) References Cited

FOREIGN PATENT DOCUMENTS

| EP | 1685816 B1 | 1/2013 |
| EP | 2024178 B1 | 1/2013 |
| EP | 2088980 B1 | 1/2013 |
| EP | 1272347 B1 | 4/2013 |
| EP | 1458565 B1 | 3/2014 |
| EP | 2727521 A1 | 5/2014 |
| EP | 1575470 B1 | 6/2014 |
| EP | 2088981 B1 | 6/2014 |
| EP | 2431013 B1 | 9/2014 |
| EP | 2441866 B1 | 2/2015 |
| EP | 2133297 B1 | 4/2016 |
| EP | 1806117 B1 | 6/2016 |
| EP | 3028687 A1 | 6/2016 |
| EP | 3092997 A1 | 11/2016 |
| EP | 1666178 B1 | 5/2017 |
| EP | 2214614 B1 | 8/2017 |
| EP | 2450015 B1 | 11/2017 |
| EP | 2105115 B1 | 3/2018 |
| EP | 3299167 A1 | 3/2018 |
| EP | 2116367 B1 | 4/2018 |
| EP | 2142261 B1 | 5/2018 |
| EP | 2454957 B1 | 11/2018 |
| EP | 3117810 B1 | 7/2019 |
| EP | 3527181 A1 | 8/2019 |
| EP | 3199132 B1 | 9/2019 |
| EP | 3056176 B1 | 10/2019 |
| EP | 3296100 B1 | 1/2020 |
| EP | 3646830 A1 | 5/2020 |
| EP | 3677231 A1 | 7/2020 |
| EP | 3747636 A1 | 12/2020 |
| EP | 3558192 B1 | 1/2021 |
| EP | 3558664 B1 | 4/2021 |
| EP | 3519162 B1 | 7/2021 |
| EP | 3572052 B1 | 7/2021 |
| EP | 3558193 B1 | 8/2021 |
| EP | 3865103 A1 | 8/2021 |
| EP | 3558191 B1 | 9/2021 |
| EP | 3275413 B1 | 10/2021 |
| EP | 3342385 B1 | 10/2021 |
| EP | 3527182 B1 | 10/2021 |
| EP | 3675785 B1 | 11/2021 |
| EP | 3904057 A1 | 11/2021 |
| EP | 3960140 A1 | 3/2022 |
| EP | 3960439 A1 | 3/2022 |
| EP | 3981371 A1 | 4/2022 |
| EP | 3675784 B1 | 10/2022 |
| FR | 2532337 A1 | 3/1984 |
| JP | 2005095574 A | 4/2005 |
| JP | 2008154998 A | 7/2008 |
| JP | 2009056156 A | * | 3/2009 |
| JP | 2009106667 A | | 5/2009 |
| JP | 5085239 B2 | | 11/2012 |
| JP | 05106990 B2 | | 12/2012 |
| JP | 05124188 B2 | | 1/2013 |
| JP | 2014198179 A | | 10/2014 |
| JP | 2017064130 A | | 4/2017 |
| JP | 06192003 B2 | | 9/2017 |
| JP | 2019030441 A | | 2/2019 |
| KR | 1982464 B1 | | 5/2019 |
| KR | 2013608 B1 | | 8/2019 |
| KR | 2022211 B1 | | 9/2019 |
| RU | 2304047 C2 | | 8/2007 |
| RU | 2010125133 A | | 12/2011 |
| WO | WO1993021788 A1 | | 11/1993 |
| WO | WO0192013 A1 | | 12/2001 |
| WO | WO2009067055 A1 | | 5/2009 |
| WO | WO2011087502 A1 | | 7/2011 |
| WO | 2014109924 A1 | | 7/2014 |
| WO | WO2014145668 A1 | | 9/2014 |
| WO | 2016033226 A1 | | 3/2016 |
| WO | 2016109514 A1 | | 7/2016 |
| WO | WO2016160752 A1 | | 10/2016 |
| WO | 2016208513 A1 | | 12/2016 |
| WO | WO2018097771 A1 | | 5/2018 |
| WO | 2018118431 A1 | | 6/2018 |
| WO | WO2018118573 A1 | | 6/2018 |
| WO | 2018/154680 A1 | | 8/2018 |
| WO | WO2018160207 A1 | | 9/2018 |
| WO | WO2018160208 A1 | | 9/2018 |
| WO | WO2019070248 A1 | | 4/2019 |
| WO | WO2019125415 A1 | | 6/2019 |
| WO | WO2020198025 A1 | | 10/2020 |
| WO | WO2021043943 A1 | | 3/2021 |

OTHER PUBLICATIONS

Grishanov et al., "Advances in the CAD Simulation of Textile Yarns", Res. J. Textile & Apparel, vol. 15, No. 1, Feb. 2011). (Year: 2011).*

Presentation by Thomas Ehlert, VP of RD&E, Aurizon Ultrasonics, LLC, entitled "Adhesive-free, Ultrasonic Elastic Attachment", date at least as early as Nov. 17, 2014, 57 pages.

Notification of Reasons for Refusal issued in Japanese Application No. 2020-147443, dated Oct. 23, 2023, 5 pages.

PCT International Search Report and Written Opinion, Jun. 4, 2021.

PCT International Search Report and Written Opinion, PCT/US2015/047015, dated Nov. 24, 2015, 8 pages.

Japanese Office Action for Application No. JP2020-541440 dated Feb. 7, 2023.

* cited by examiner

FROM CREEL

APPARATUS AND METHOD OF MANUFACTURING AN ELASTIC COMPOSITE STRUCTURE FOR AN ABSORBENT SANITARY PRODUCT

CROSS-REFERENCE TO RELATED APPLICATIONS

The present invention claims priority to U.S. Provisional Patent Application Ser. No. 62/786,609 filed Dec. 31, 2018, the disclosure of which is incorporated herein by reference in its entirety.

BACKGROUND OF THE INVENTION

Embodiments of the invention relate generally to absorbent sanitary products and, more particularly, to an improved apparatus and method for manufacturing an elastic composite structure for use in an absorbent sanitary product that minimizes or eliminates the use of consumable adhesives such as glue.

Absorbent sanitary products, such as disposable diapers, are typically equipped with elastic composite structures that include one or more elastic threads. These elastic composite structure s are positioned at various locations throughout the product, including in the waistbands, leg cuff regions, and throughout all or portions of the front or back panels of the product. During the typical manufacturing process of an elastic composite structure, the elastic threads are held in a tensioned state and an adhesive is used to secure the elastic threads between the two facing layers of non-woven materials or webs. The tension in the elastic threads is subsequently released, causing the web material to pucker or fold in the areas that contain the adhered elastic threads.

The use of adhesives to bond the elastic threads within elastic composite structure s presents a number of disadvantages in both the end product and manufacturing method, including costs associated with the consumable material and undesirable tactile properties of the end product (e.g., stiffness). While thermal or ultrasonic welding techniques been proposed as alternatives for bonding elastic threads within an elastic composite structure, the elastic threads are prone to break during the thermal or ultrasonic bonding procedure. When a break occurs upstream of the bonding assembly, the broken elastic thread snaps back toward the feeder or creel and must be manually rethreaded before manufacture can be resumed.

Accordingly, there is a need for an improved apparatus and method for fabricating an elastic composite structure of an absorbent sanitary product that minimizes or eliminates machine downtime in the event that an elastic thread breaks during manufacture. It would further be desirable for such an apparatus and method to eliminate or minimize the use of consumable adhesives to secure the elastic threads to the facing web layers.

BRIEF DESCRIPTION OF THE INVENTION

In accordance with one aspect of the invention, an apparatus for manufacturing an elastic composite structure includes at least one structure configured to guide a first web layer and a second web layer in a machine direction, an elastic thread combiner configured to combine a plurality of elastic threads to form a combined elastic thread assembly, and a bonding unit. The bonding unit is configured to bond the first web layer to the second web layer via a bond pattern comprising a plurality of bond lines each having at least one pair of adjacent bonds and anchor the combined elastic thread assembly within a passage defined by a pair of adjacent bonds in each of the plurality of bond lines. The passage is narrower than the combined elastic thread assembly in a non-tensioned state and wider than one of the plurality of elastic threads in a non-tensioned state.

In accordance with another aspect of the invention, a method of manufacturing an elastic composite structure includes positioning an elastic thread assembly between a first web layer and a second web layer, the elastic thread assembly comprising a plurality of elastic threads. The method also includes bonding the first web layer to the second web layer via a bond pattern comprising a plurality of bond lines having pairs of adjacent bonds and anchoring the elastic thread assembly within a passage formed between the first web layer and the second web layer, the passage defined between facing edges of pairs of adjacent bonds in the plurality of bond lines. The facing edges are spaced apart by a distance that is smaller than an overall diameter of the elastic thread assembly in a non-tensioned state and that is larger than a strand diameter of the plurality of elastic threads in a non-tensioned state.

In accordance with another aspect of the invention, an elastic composite structure includes a first web layer and a second web layer coupled to the first web layer by a bond pattern comprising a plurality of bond lines, each bond line having at least one pair of adjacent bonds. The elastic composite structure also includes an elastic thread assembly comprising a plurality of elastic threads extending through a passage defined by facing edges of the pairs of adjacent bonds of the bond lines. The facing edges of the pairs of adjacent bonds are spaced apart a by distance that is smaller than an overall diameter of the elastic thread assembly in a non-tensioned state and that is larger than a strand diameter of an elastic thread of the plurality of elastic threads in a non-tensioned state.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings.

DETAILED DESCRIPTION

Embodiments of the present invention provide for a method and apparatus for manufacturing an elastic composite structure usable in an absorbent sanitary product such as, for example, a diaper, disposable adult pant, or feminine care product.

During the manufacture of absorbent sanitary products, it is often desirable to secure elastic threads between facing layers of non-woven material to form contoured or elasticized regions within the product. Such products are typically manufactured on an assembly or manufacturing line in which the product moves substantially continually longitudinally in what is referred to as the "machine direction."

Figure 1:
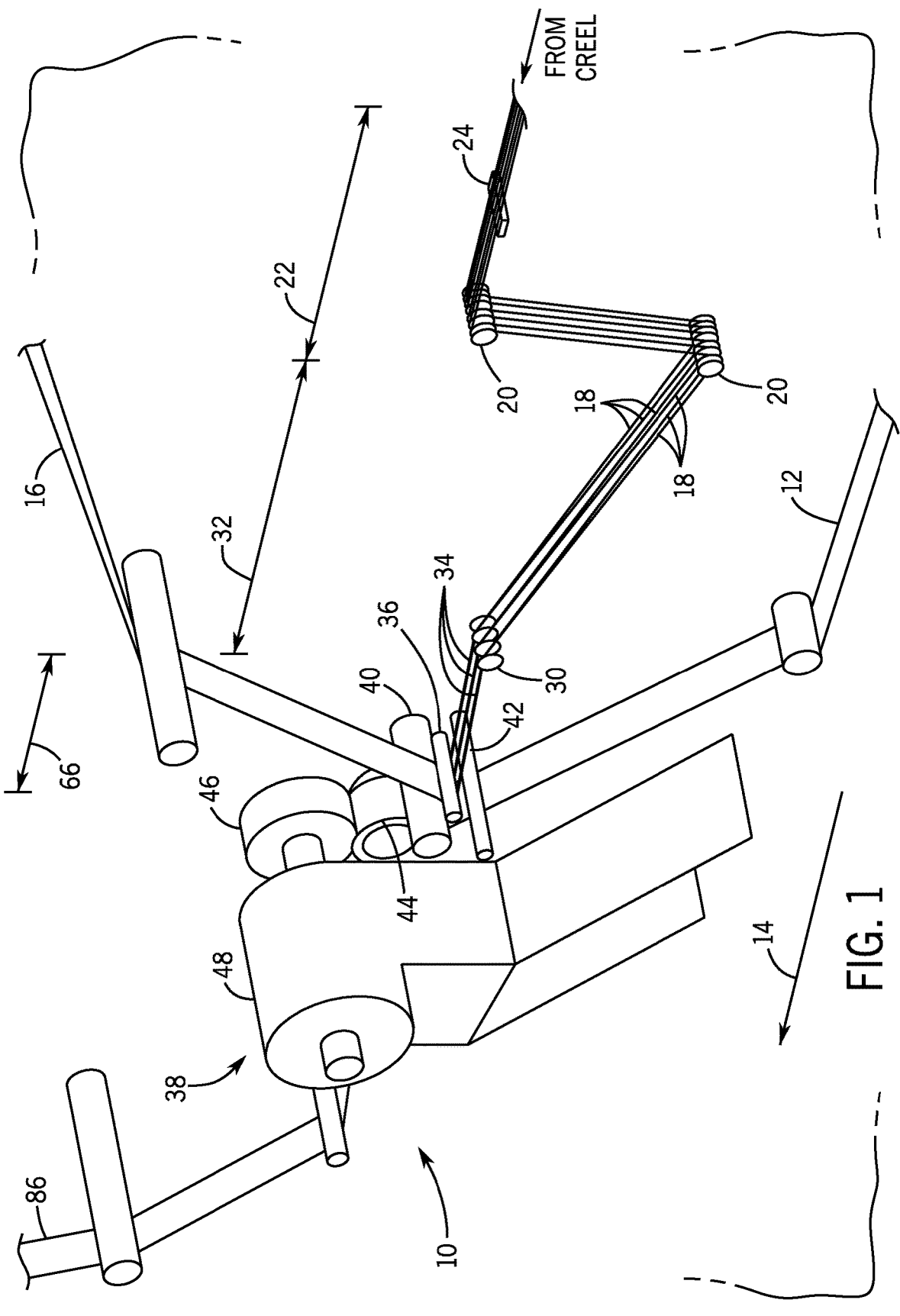
FIG. 1 is a schematic perspective view of a portion of a manufacturing line for fabricating an elastic composite structure.

Referring now to FIG. 1, a portion of an exemplary manufacturing line 10 is illustrated according to one embodiment of the invention. As shown, a first web layer 12 is fed in the machine direction 14. A second web layer 16 is similarly fed in the machine direction 14. First web layer 12 and second web layer 16 are materials capable of fusing to one another upon application of an applied energy that causes one or both of the webs 12, 16 to soften or melt and join together. First and second web layers 12, 16 may be the same type of material or different materials according to alternative embodiments. As non-limiting examples, first and second web layers 12 may include nonwoven materials, woven materials, films, foams, and/or composites or laminates of any of these material types.

A series of individual elastic threads 18 are positioned between the first and second web layers 12, 16. The elastic threads 18 travel in the machine direction 14 under tension from a creel assembly (not shown) or similar device. The elastic threads 18 may be composed of any suitable elastic material including, for example, sheets, strands or ribbons of thermoplastic elastomers, natural or synthetic rubber, or LYCRA, as non-limiting examples. Each elastic thread 18 may be provided in the form of an individual elastomeric strand or be a manufactured multifilament product that includes many individual elastomeric filaments joined together, such as by a dry-spinning manufacturing process, to form a single, coalesced elastic thread 18. Each elastic thread 18 may be in the range of approximately 200-1500 decitex (dTex), in non-limiting embodiments. In an embodiment where an elastic thread 18 is a multifilament product, the elastic thread 18 may have an overall decitex of 400 dTex, in an exemplary and non-limiting embodiment, with the individual elastomeric filaments of the elastic thread 18 individually having a decitex of ten percent or less of the overall 400 dTex value.

Figure 7:
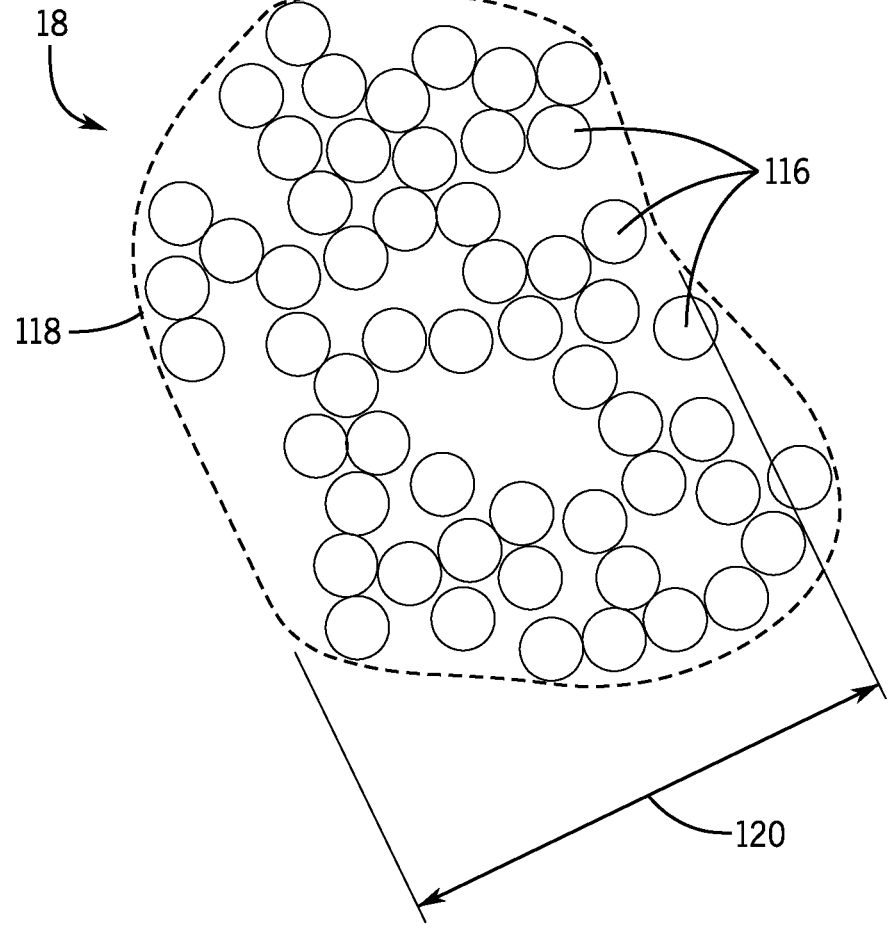
FIG. 7 is a cross-sectional view of a multifilament elastic thread usable to manufacture the elastic composite of FIG. 5.

Elastic threads 18 may have any suitable cross-sectional shape that facilitates formation of an elastic composite structure having desired elasticity, visual aesthetic, and manufacturability. As non-limiting examples, elastic threads 18 may have a cross-sectional shape that is round, rectangular, square, or irregular as may be the case where each elastic thread 18 is a multifilament product (as illustrated in detail in FIG. 7).

While first web layer 12 and second web layer 16 are depicted in FIG. 1 and described herein as physically separate components, it is contemplated that alternative embodiments may utilize a unitary web structure that is folded to capture the elastic threads 18 between upper and lower layers of the unitary web structure.

Manufacturing line 10 includes one or more guide rollers 20 that are employed to accurately position and tension the elastic threads 18 during a first distance of travel 22 in the machine direction 14. In some embodiments, manufacturing line 10 may include one or more optional tension monitoring devices 24 (shown in phantom) that are positioned along the path of travel of the elastic threads 18. In such an embodiment, feedback from the tension monitoring devices 24 may be utilized to control the tension (i.e., elongation) in the elastic threads 18 as they travel in the machine direction 14.

Figure 2:
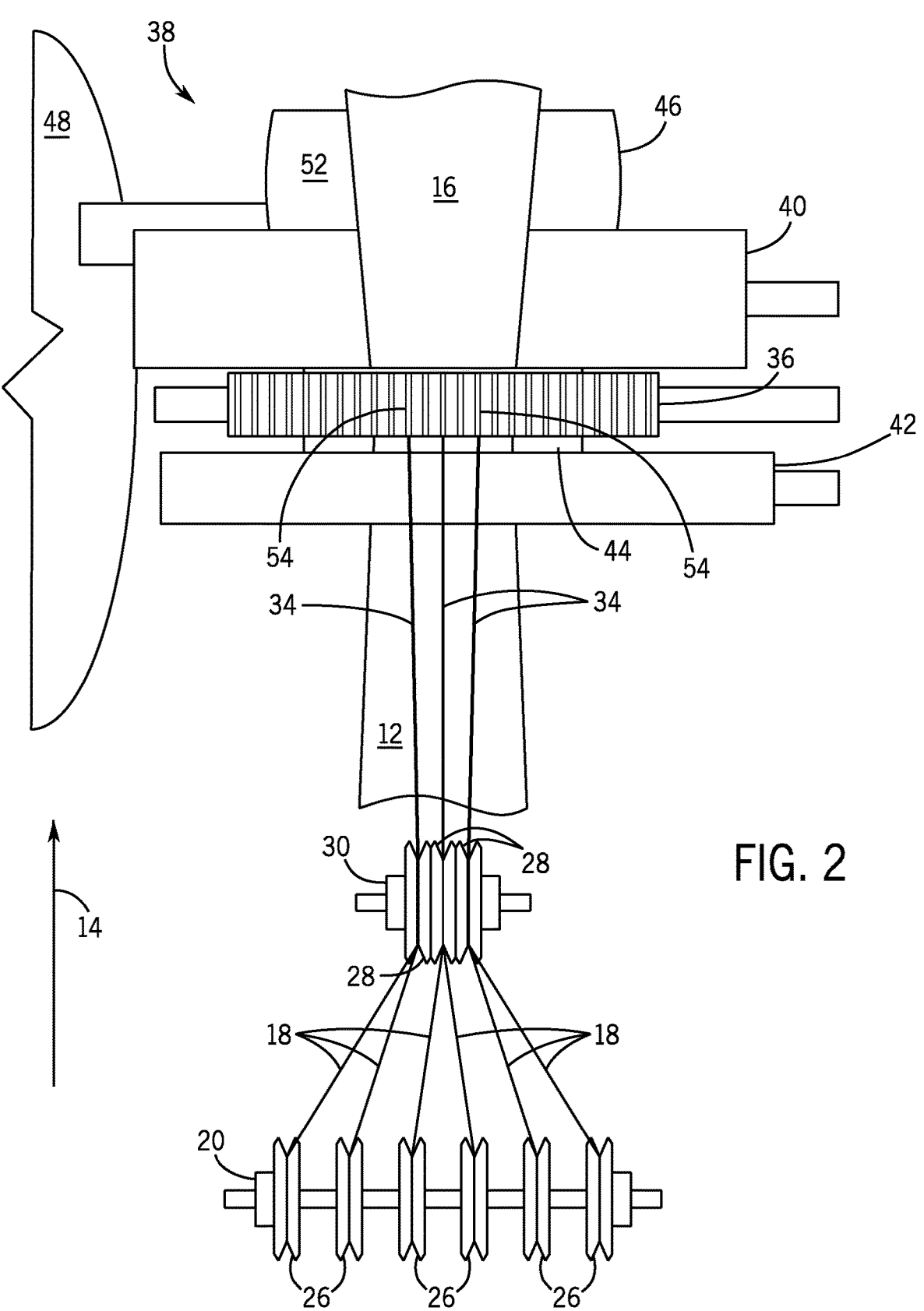
FIG. 2 is a schematic perspective view of a portion of the manufacturing line illustrated in FIG. 1.

As shown in further detail in FIG. 2, each respective elastic thread 18 is positioned within a respective guiding section 26 of guide rollers 20. Doing so maintains separation between the adjacent elastic threads 18 throughout the first distance of travel 22 (FIG. 1) of the manufacturing line 10. In the illustrated embodiment, guiding section 26 includes notches that aid in alignment and guiding of the elastic threads 18. Notches may be v-shaped as shown, have curved or other alternative geometries, or be omitted entirely in alternative embodiments. In yet other embodiments, guide rollers 20 may be replaced by any other known type of device that is configured to align and guide elastic threads. Referring now to FIG. 1 and FIG. 2 together as appropriate, multiple adjacent elastic threads 18 are fed in the machine direction 14 toward a common combining section 28 of an elastic thread combiner or combining guide roller 30 throughout a second distance of travel 32 of the manufacturing line 10. The adjacent elastic threads 18 are combined or grouped together at the common combining section 28 to form a combined elastic thread assembly 34, which includes a number of individual elastic threads 18.

While only one combining guide roller 30 is shown in FIGS. 1 and 2, it is contemplated that alternative embodiments may include any number of multiple combining guide rollers 30 depending upon design considerations (e.g., the size and spacing of the total number of elastic threads 18 in the end product). Similarly, alternative embodiments may include one or more guide rollers 20 at any given point along the manufacturing line 10.

In the illustrated embodiment, two (2) adjacent elastic threads 18 are combined together at a common combining section 28 to form a combined elastic thread assembly 34. Similar to guiding section 26 of guide rollers 20, each combining section 28 may include a notch that aid in alignment and guiding of the respective combined elastic thread assemblies 34. Notches may be v-shaped as shown, have curved or other alternative geometries, or be omitted entirely in alternative embodiments. In yet other embodiments, combining guide roller 30 may be replaced by any other known type of device that is configured to combine multiple elastic threads.

While two elastic threads 18 are shown grouped to form combined elastic threads 34 for clarity, it is understood that any number of multiple threads may be combined within a common combining section 28 to form respective groupings of combined elastic threads 34, with the total number of elastic threads 18 in a given combined elastic thread assembly 34 determined based on design specifications. As just one non-limiting example, two 600 dTex elastic threads 18 or three 400 dTex elastic threads 18 may be combined together to form a combined elastic thread assembly 34 having an overall decitex value of 1200. Grouping more than two (2) elastic threads 18 together to form a combined elastic thread assembly 34 enhances the self-rethreading capability of an individual elastic threads 18 in the event of a break, as described in further detail below. It will also be understood that, while FIG. 1 depicts three (3) combined elastic thread assemblies 34, the techniques disclosed herein may be extended for the manufacture of an elastic composite structures that includes a single combined elastic thread assembly or any number of multiple combined elastic thread assemblies.

Together guide rollers 20 and combining guide roller assembly 30 operate to accurately position and tension individual elastic threads 18 and the combined elastic thread assemblies 34 as they travel through the first and second distances of travel 22, 32 toward a strand guide roller 36 that is positioned upstream of a bonding unit 38, which is referred to hereafter as an ultrasonic bonding assembly or apparatus 38. Manufacturing line 10 also includes one or more structures that are configured to guide the first and second web layers 12, 16 in the machine direction 14. In the illustrated embodiment, these guide structures include an upper roller 40 and a lower roller 42 are positioned to guide the first web layer 12 and the second web layer 16, respectively, toward the ultrasonic bonding apparatus 38.

Ultrasonic bonding apparatus 38 may be a rotary ultrasonic welding system or a blade ultrasonic welding system in alternative embodiments. In the illustrated embodiment, ultrasonic bonding apparatus 38 is a rotary ultrasonic welding system that includes a rotary anvil 44 and a horn 46 that cooperate with each other to bond the first web layer 12 to the second web layer 16. The combined elastic thread assemblies 34 are secured or anchored in position relative to the first and second web layers 12, 16 as described in detail below. Ultrasonic bonding apparatus 38 also includes one or more frames 48 that support and/or house a motor (not shown) that drives the horn 46, a vibration control unit (not shown) that causes the horn 46 to vibrate, and a second motor (not shown) that drives the anvil 44. The horn 46 and anvil 44 are positioned in a spaced relationship relative to one another to facilitate ultrasonically bonding the first and second web layers 12, 16 to one another while the combined elastic thread assemblies 34 are held in tension in the space between the horn 46 and anvil 44. While horn 46 is illustrated as a rotary horn in FIG. 1, a stationary horn may be used in alternative embodiments.

The face 50 of the anvil 44 includes an arrangement of projections and notches that facilitate securing the combined elastic thread assemblies 34 in position relative to the first and second web layers 12, 16. One exemplary embodiment of this arrangement of projections and notches is described in detail below relative to FIG. 4. However, it is contemplated that anvil face 50 may include any number of alternative arrangements of projections and notches that transfers a desired bonding pattern onto first and second web layers 12, 16 in a manner that securely anchors the combined elastic thread assemblies 34 in position between the first and second web layers 12, 16.

In one non-limiting embodiment, the face 52 of the horn 46 has a smooth or substantially smooth surface contour. In alternative embodiments, face 52 may include an arrangement of projections and/or notches that mate or align with the surface pattern of the anvil 44 to further facilitate bonding the first and second web layers 12, 16 together and securing the combined elastic thread assemblies 34 in position relative to the first and second web layers 12, 16.

While embodiments of the invention are described relative to an ultrasonic bonding assembly and ultrasonic bonding technique, it is contemplated that the techniques described herein may be extended to any other known thermal or pressure bonding techniques. In yet other alternative embodiments, ultrasonic bonding apparatus 38 may be replaced with one or more adhesive applicators that is/are configured to secure the combined elastic thread assemblies 34 to the first and second web layers 12, 16 in a tensioned state via adhesive. Such an embodiment would utilize known adhesive applicating technologies while leveraging the self-rethreading benefits of combining guide roller 30.

FIG. 2 is a view of a portion of the manufacturing line 10 upstream of the ultrasonic bonding apparatus 38 looking into the machine direction 14. As shown, the individual elastic threads 18 are fed outward from respective guiding sections 26 in the guide rollers 20. Multiple individual elastic threads 18 are fed into a common combining section 28 of the combining guide roller assembly 30, thereby forming multiple combined elastic thread assemblies 34. Each combined elastic thread assembly 34 is then fed toward strand guide roller 36. In the embodiment, strand guide roller 36 includes an array of notches 54 that aid in aligning and guiding the combined elastic thread assemblies 34 as they are received between the horn 46 and anvil 44. These notches 54 may be evenly spaced across all of the strand guide roller 36 in the manner shown or may span only a portion thereof in an alternative embodiment. In yet other embodiments, the notches 54 may be positioned at uneven intervals along the length of strand guide roller 36 depending upon design specifications and the desired placement and spacing of the combined elastic thread assemblies 34 in the resulting elastic composite structure.

Figure 3:
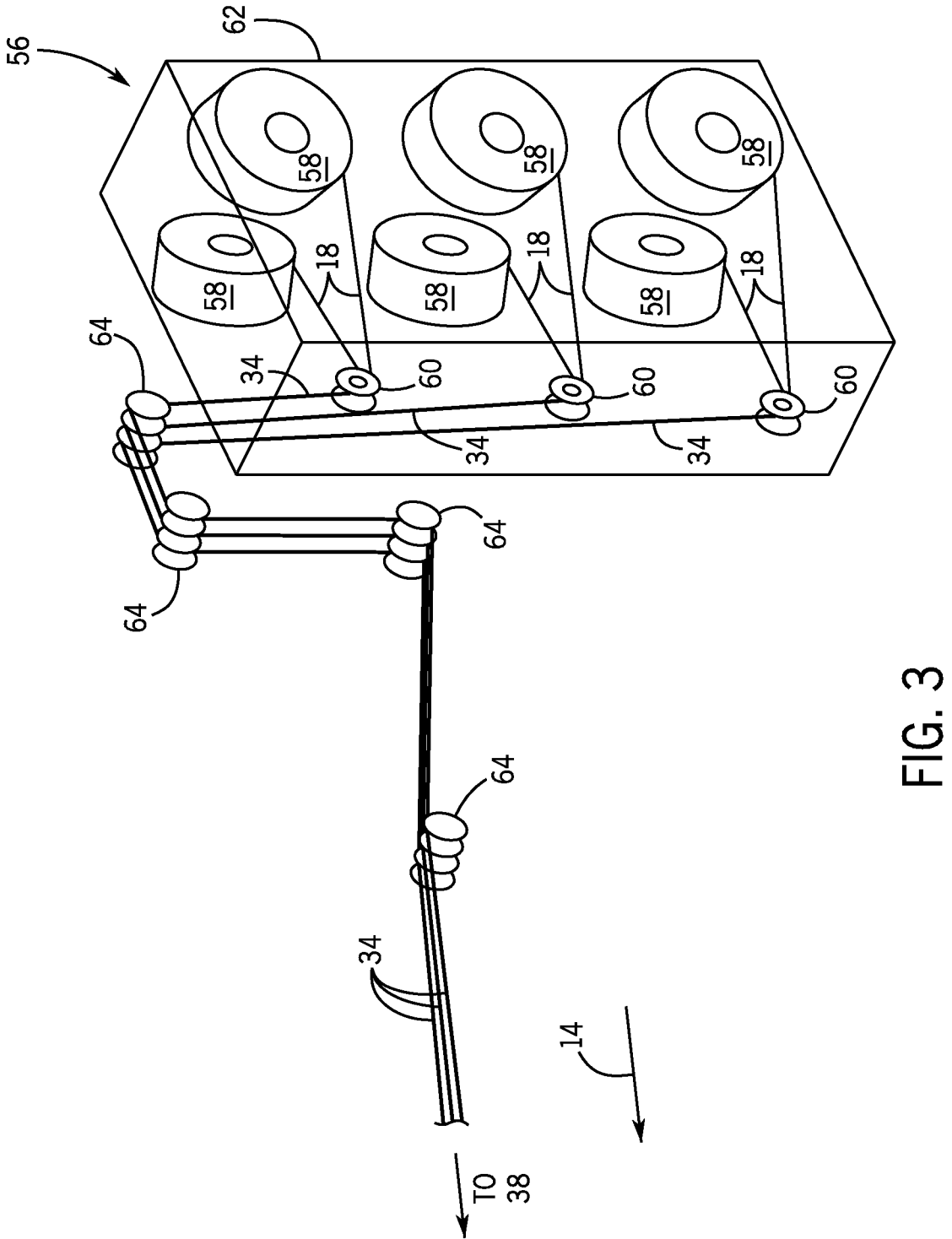
FIG. 3 is a perspective view of a creel assembly usable with the manufacturing line of FIG. 1.

In the embodiment described above, the combining guide roller assembly 30 is used to combine the individual elastic threads 18 into groupings of multiple combined elastic thread assemblies 34. In an alternative embodiment, individual elastic threads 18 are combined into groups of combined elastic thread assemblies 34 within a creel assembly 56 as illustrated in FIG. 3. As shown, individual elastic threads 18 are unwound from strand rolls 58 using reels, which are not separately depicted in FIG. 3. Multiple individual elastic threads 18 are fed into a common feeder 60 that is either contained within or mounted to the frame 62 of the creel assembly 56. Again, for clarity purposes two (2) elastic threads 18 are shown as being grouped together within creel assembly 56 to form each combined elastic thread assemblies 34. However, it is understood that any number of multiple elastic threads 18 may be combined at each feeder 60 to form respective combined elastic thread assemblies 34. The combined elastic thread assemblies 34 exit creel assembly 56 and are directed across one or more guide rollers 64, which may be constructed in any similar manner as described with respect to guide rollers 20 of FIG. 1 and position and tension the combined elastic thread assemblies 34 as they enter the first distance of travel 22 of the manufacturing line 10 of FIG. 1.

In existing ultrasonic bonding systems, the most common points of breakage of an individual elastic thread are (A) in the space between the horn 46 and the anvil 44 and (B) upstream of the ultrasonic bonding apparatus 38. When breakage occurs upstream of the ultrasonic bonding apparatus 38, the broken elastic thread snaps back toward the creel assembly since each elastic thread travels along the manufacturing line 10 under tension. When a broken strand snaps back, it often causes additional strands to break, especially in the case of full-panel products that may include 100 or more individual strands. When a break and snap back occurs, production must be halted until the broken elastic thread is rethreaded through the various guide rollers—a process which may take hours or the remainder of a given shift. These delays significantly reduce the product output of a given assembly line and result in considerable lost scrap material during the initial shutdown process and again at line startup.

In both of the above-described embodiments of forming a combined elastic thread assembly 34, elastic threads 18 enter the ultrasonic bonding apparatus 38 as part of a combined elastic thread assembly 34 rather than as a discrete, individual elastic thread 18 that is physically spaced apart from other elastic threads 18 in the cross-machine direction. Should one of the elastic threads 18 of a given combined elastic thread assembly 34 break at or before it enters the ultrasonic bonding apparatus 38, the broken elastic thread 18 will snap back to a downstream location where it will grip or wrap around at least one other elastic thread 18 within its original combined elastic thread assembly 34. In an embodiment that includes combining guide roller assembly 30, the broken elastic thread 18 of a given combined elastic thread assembly 34 will snap back to a location upstream of the combining guide roller assembly 30. In an embodiment where the elastic threads 18 are combined at respective feeders 60 of creel 56, the broken elastic thread 18 will snap back to some point downstream of the feeder 60. In either case, friction between the broken elastic thread 18 and the remaining one or more elastic threads 18 of the original combined elastic thread assembly 34 will carry the broken strand 18 in the machine direction 14 toward and through the ultrasonic bonding apparatus 38. As a result, the broken elastic thread 18 will effectively self-rethread, thereby eliminating the need for an operator to halt production and manually rethread the broken elastic thread 18.

In embodiments where the elastic threads 18 are combined at the combining guide roller assembly 30, the distance between the combining guide roller assembly 30 and the ultrasonic bonding apparatus 38 (referred to hereafter as the third path of travel 66) may be defined based on the elasticity of the elastic threads 18 and tension under which those elastic threads 18 is maintained during operation to enhance the probability that the snapback point of a broken strand elastic threads 18 will occur at a point along the third path of travel 66.

Figures 4, 4A:
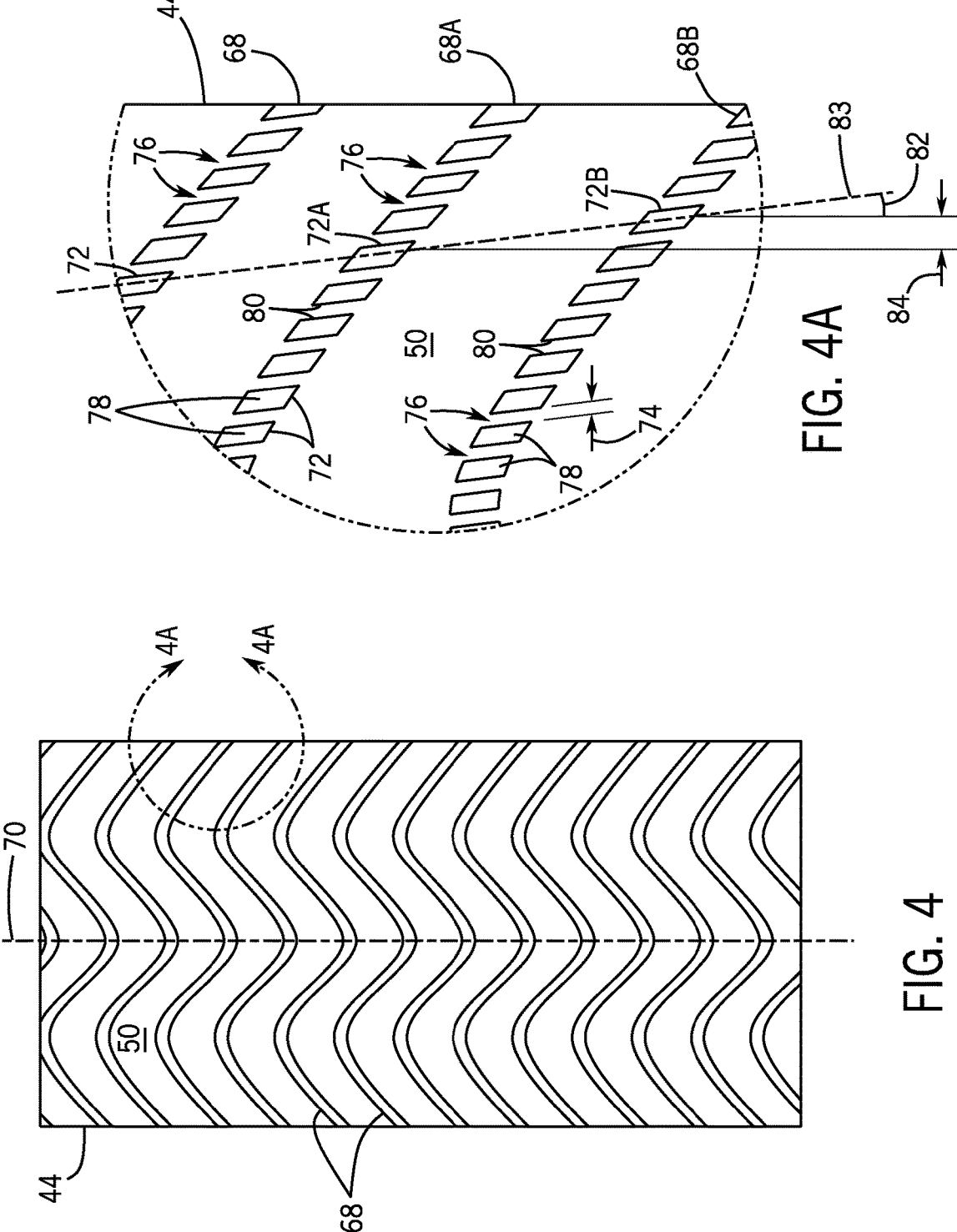
FIG. 4 is a front view of a rotary anvil usable with the manufacturing line of FIG. 1, according to an embodiment of the invention.
FIG. 4A is a detailed view of a portion of the rotary anvil of FIG. 4.

Referring now to FIG. 4, further details of the surface pattern of the anvil 44 is provided in accordance with one non-limiting embodiment of the invention. As shown, anvil 44 includes an array of welding lines 68 that are spaced apart from one another along the circumferential axis 70 of the anvil face 50. As shown more specifically in the detailed view provided in FIG. 4A, each welding line 68 contains a pattern of discrete projections 72 that extend outward from the face 50 of the anvil 44. The projections 72 are evenly spaced apart from one another, thereby defining a uniform width gap 74 in each of the notches 76 that is formed between adjacent projections 72. Welding lines 68 are sinusoidal in the embodiment shown. However, may be straight lines, curved lines, or otherwise arranged to create a continuous and repeating pattern on the end product.

In the illustrated embodiment, the contact surfaces 78 of the projections 72 have side surfaces 80 oriented at an angle 82 relative to the circumferential axis 70 such that no hypothetical arc 83 drawn from adjacent welding lines 68 is parallel to the circumferential axis 70 of the anvil 44. In such an embodiment, the facing surfaces 80 of adjacent projections 72 are non-parallel to the circumferential axis 70 as shown. As a result, projections 72 of adjacent welding lines 68 are not aligned with one another along the circumferential axis 70. Instead, a given projection 72A in one welding line 68A is offset from a given projection 72B in an adjacent welding line 68B by a pitch 84 defined by an angle 82. Projections 72 thus define a threaded pattern that extends around the circumferential face 50 of the anvil 44.

It is contemplated that the contact surfaces 78 of the projections 72 may have different geometries in alternative embodiments. As non-limiting examples, projections 72 may be circular, rectangular, crescent shaped, or have irregular shapes that may be selected to form a desired overall pattern on the end product. In yet another embodiment, corresponding projections 72A, 72B of adjacent welding lines 68A, 68B may be aligned with one another in a line parallel to the circumferential axis 70. Alternatively, projections 72A, 72B of sequential welding lines 68A, 68B may be offset from one another in the cross-machine direction thereby defining a stepped or non-linear passage through the bond lines that are formed on the first and second web layers 12, 16.

Figures 5, 5A:
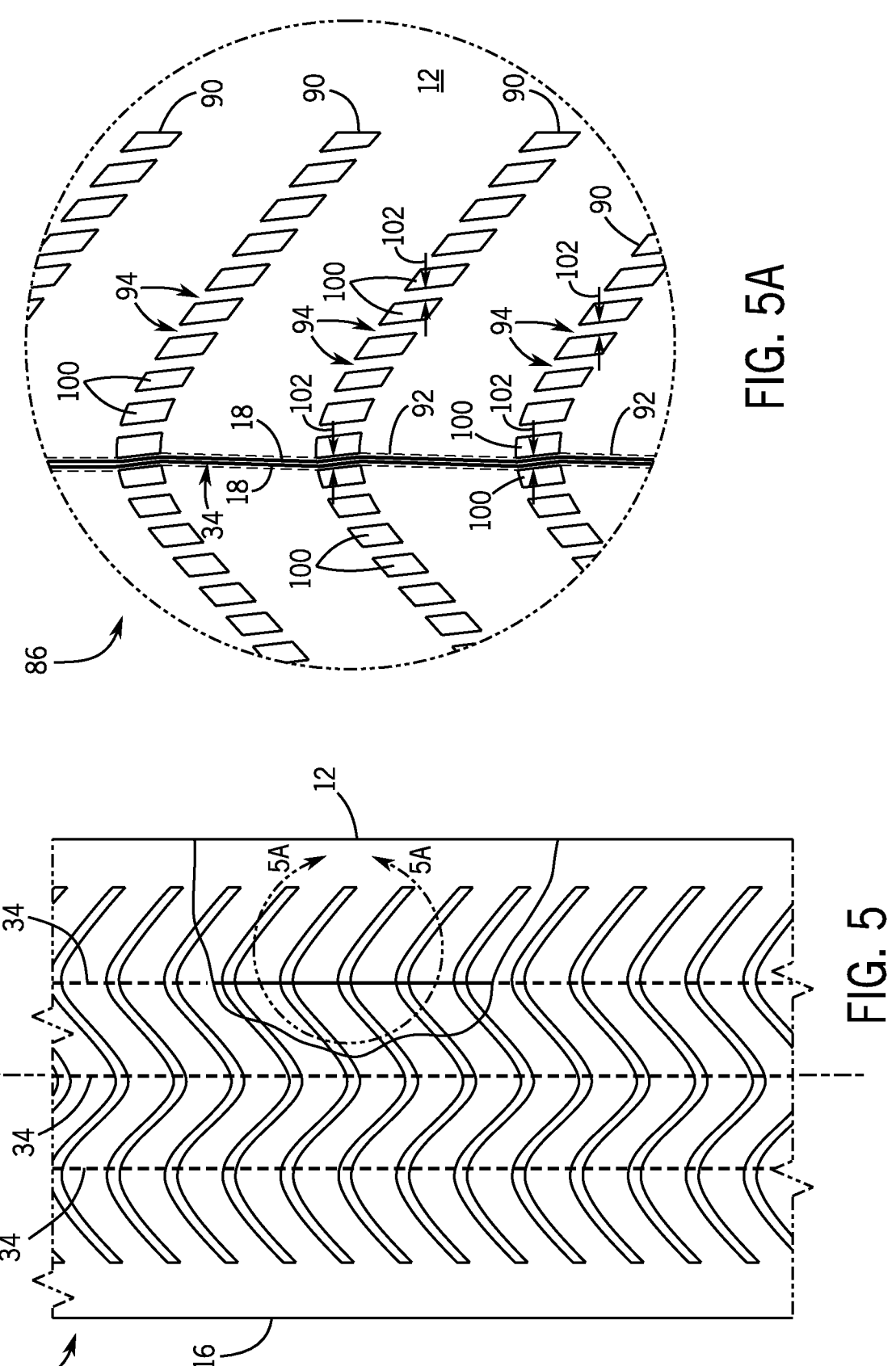
FIG. 5 is a top view of a portion of an elastic composite structure shown in an elongated state, according to an embodiment of the invention.
FIG. 5A is a detailed view of a portion of the elastic composite structure of FIG. 5 shown in the elongated state.

FIG. 5 illustrates a portion of an elastic composite structure 86 output from the ultrasonic bonding apparatus 38. The elastic composite structure 86 is illustrated in an elongated state with individual elastic threads 18 of the combined elastic thread assemblies 34 stretched to a point where the first web layer 12 and second web layer 16 are substantially flat. As shown, the elastic composite structure 86 includes the first web layer 12, the second web layer 16, and a number of combined elastic thread assemblies 34 that are located between the first and second web layers 12, 16 and oriented along a longitudinal axis 88 of the elastic composite structure 86. While the illustrated embodiment includes three (3) combined elastic thread assemblies 34 it is contemplated that alternative embodiments may include a single combined elastic thread assembly 34 or any number of multiple combined elastic thread assemblies 34 based on design specifications of the end product.

The ultrasonic bonding operation results in a continuous and repeating pattern of bond lines 90 that mirror the welding lines 68 on the anvil 44 and bond or fuse the first web layer 12 to the second web layer 16. Thus, in embodiments where welding lines 68 are sinusoidal, the resulting bond lines 90 have a similar sinusoidal bond pattern. As shown in the detailed view provided in FIG. 5A, the tensioned elastic threads 18 of a given assembly of combined elastic threads 34 extends along a passage 92 that is bounded by the gap 94 formed between the facing edges 96, 98 of a pair of adjacent bonds 100 in each subsequent bond line 90. The gap 94 has a width 102 that mirrors the width 74 of the notches 76 on the anvil 44.

Figures 6A, 6B:
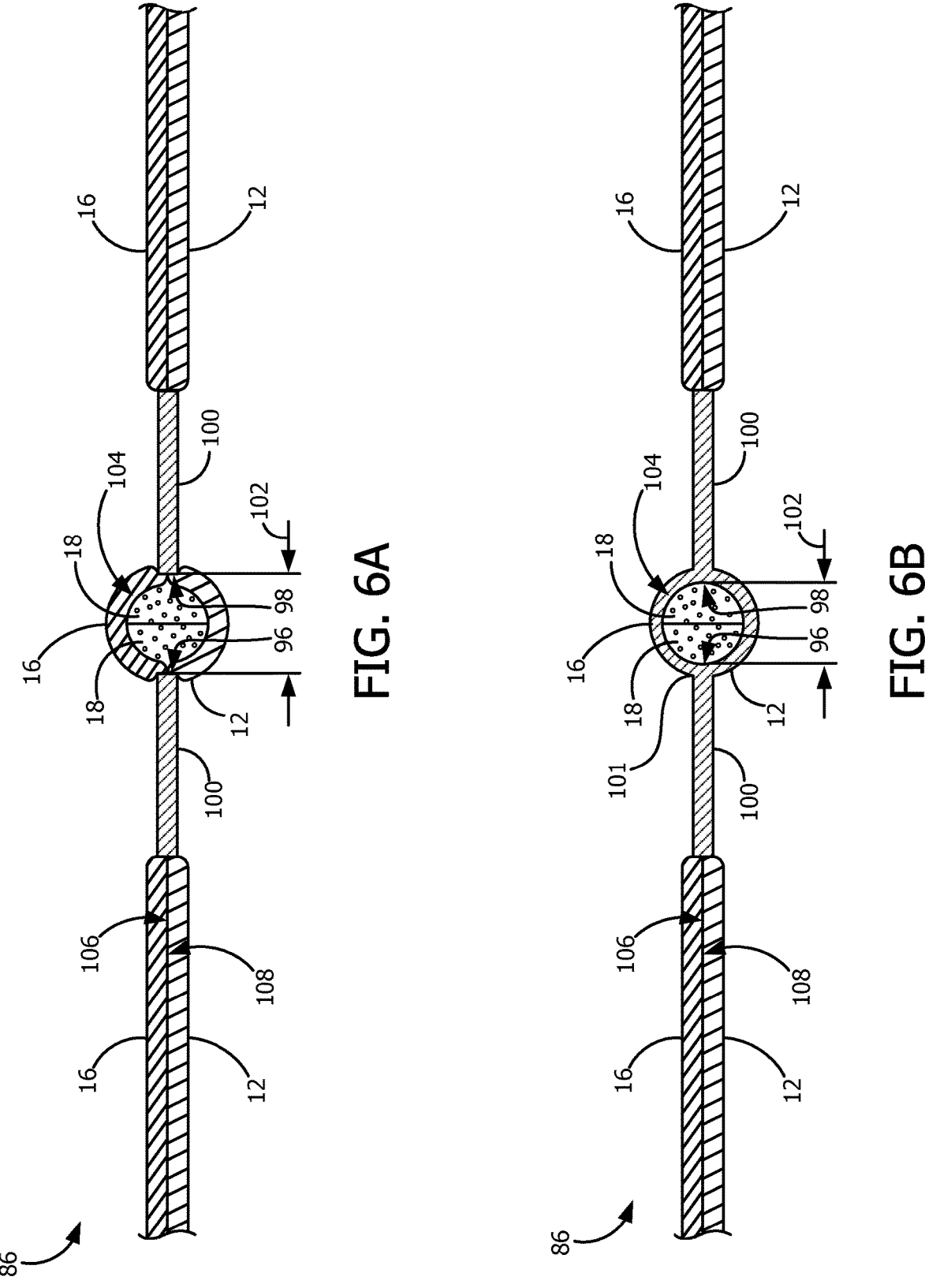
FIG. 6A is a cross-sectional view of a portion of the elastic composite structure of FIG. 5 in the relaxed state, according to one embodiment of the invention.
FIG. 6B is a cross-sectional view of a portion of the elastic composite structure of FIG. 5 in the relaxed state, according to another embodiment of the invention.

When the elastic composite structure 86 is permitted to relax, each of the individual elastic threads 18 within each combined elastic thread assembly 34 will attempt to swell or expand to return to its non-tensioned or relaxed state. As shown in FIGS. 6A and 6B, as the individual elastic threads 18 expand, they become anchored or trapped in the void 104 formed between the upward facing surface 106 of the first web layer 12, the downward facing surface 108 of the second web layer 16, and the facing edges 96, 98 of a pair of adjacent bonds 100.

Depending on the operating parameters of the ultrasonic bonding apparatus 38 and/or the geometry and configuration of the notches and projections on the anvil and/or horn, the resulting pair of adjacent bonds 100 either may be discrete, discontinuous bonds 100, as shown in FIG. 6A, or part of a continuous fusion bond 101 that fuses the facing web layers 12, 16 together at bond points 100 and fuses one or both of the facing web layers 12, 16 to the combined elastic thread assembly 34, as shown in FIG. 6B.

Figure 5B:
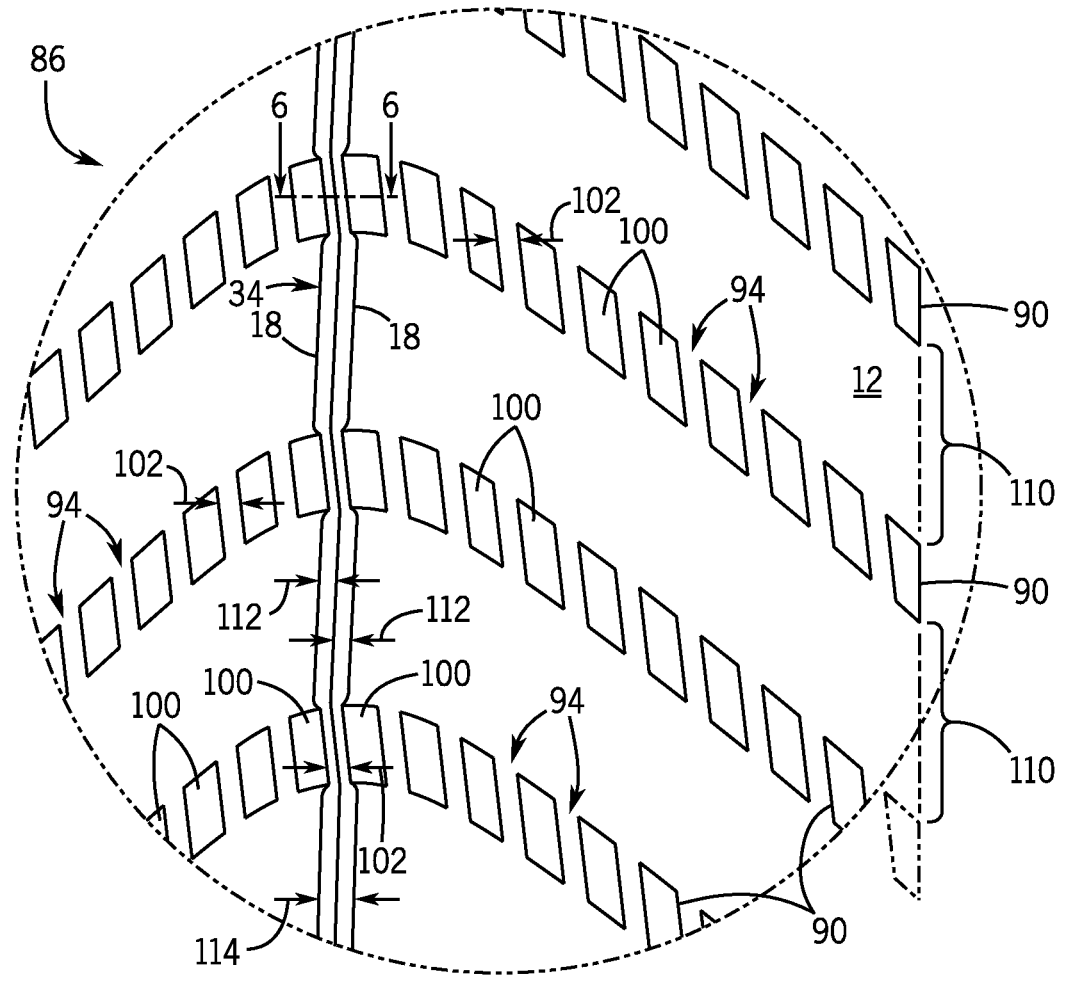
FIG. 5B is a detailed view of a portion of the elastic composite structure of FIG. 5 shown in a relaxed state.

Referring back to FIG. 5B, in the regions 110 between the bond lines 90, the elastic threads 18 are free to swell or expand to their non-tensioned state. In their non-tensioned state, each elastic thread 18 has a strand diameter 112 that is less than the width 102 of the gaps 94 formed between each pair of adjacent bonds 100. The overall diameter 114 of the combined elastic thread assemblies 34 while in the non-tensioned state is greater than the width 102 of the gaps 94. As a result, the combined elastic thread assemblies 34 are trapped or anchored between adjacent pairs of bonds 100.

As used herein the phrase "strand diameter" refers to the smallest measurable cross-sectional width of the elastic thread 18 in its non-tensioned state. In embodiments where a given elastic thread 18 is a monofilament structure, the strand diameter is the minor diameter or smallest measurable width of the monofilament structure in its non-tensioned state. In embodiments where a given elastic thread 18 is a structure that includes many individual filaments 116 (i.e., elastic thread 18 is a multi-filament structure), the elastic thread 18 typically will have an irregular cross-sectional area 118 similar to that shown in FIG. 7. The strand diameter of such a multifilament structure is to be understood as the smallest distance 120 between opposite edges of an outline that generally defines the irregular cross-sectional area 118.

The apparatus and methods described herein can be used to make elastic composite structures for waist regions, below-waist regions, leg regions, and/or leg cuff regions of a single-piece or three-piece diaper, as non-limiting examples, without the use of glue. By eliminating the use of glue, the resulting elastic composite is softer to the touch and has a more uniform ruffling pattern in the cross-machine direction (i.e., the direction perpendicular to the machine direction). From a manufacturing standpoint, the act of incorporating multiple elastic threads within each elastic passage of the elastic composite structure provides for a more durable end product and minimizes machine down time as broken elastic threads self-rethread as they are carried along in the machine direction by the remaining unbroken elastic thread(s) within their original combined elastic assembly. Accordingly, embodiments of the invention disclosed herein provide a lower cost, more reliable manufacturing process than existing prior art approaches and result in a lower cost end product that is visually and tactilely more pleasing to the end customer.

Therefore, according to one embodiment of the invention, an apparatus for manufacturing an elastic composite structure includes at least one structure configured to guide a first web layer and a second web layer in a machine direction, an elastic thread combiner configured to combine a plurality of elastic threads to form a combined elastic thread assembly, and a bonding unit. The bonding unit is configured to bond the first web layer to the second web layer via a bond pattern comprising a plurality of bond lines each having at least one pair of adjacent bonds and anchor the combined elastic thread assembly within a passage defined by a pair of adjacent bonds in each of the plurality of bond lines. The passage is narrower than the combined elastic thread assembly in a non-tensioned state and wider than one of the plurality of elastic threads in a non-tensioned state.

According to another embodiment of the invention, a method of manufacturing an elastic composite structure includes positioning an elastic thread assembly between a first web layer and a second web layer, the elastic thread assembly comprising a plurality of elastic threads. The method also includes bonding the first web layer to the second web layer via a bond pattern comprising a plurality of bond lines having pairs of adjacent bonds and anchoring the elastic thread assembly within a passage formed between the first web layer and the second web layer, the passage defined between facing edges of pairs of adjacent bonds in the plurality of bond lines. The facing edges are spaced apart by a distance that is smaller than an overall diameter of the elastic thread assembly in a non-tensioned state and that is larger than a strand diameter of the plurality of elastic threads in a non-tensioned state.

According to yet another embodiment of the invention, an elastic composite structure includes a first web layer and a second web layer coupled to the first web layer by a bond pattern comprising a plurality of bond lines, each bond line having at least one pair of adjacent bonds. The elastic composite structure also includes an elastic thread assembly comprising a plurality of elastic threads extending through a passage defined by facing edges of the pairs of adjacent bonds of the bond lines. The facing edges of the pairs of adjacent bonds are spaced apart a by distance that is smaller than an overall diameter of the elastic thread assembly in a non-tensioned state and that is larger than a strand diameter of an elastic thread of the plurality of elastic threads in a non-tensioned state.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A method of manufacturing an elastic composite structure comprising:

positioning an elastic thread assembly between a first web layer and a second web layer, the elastic thread assembly comprising a plurality of unbonded multifilament elastic threads;

bonding the first web layer to the second web layer via a bond pattern comprising a plurality of bond lines having pairs of adjacent bonds;

anchoring the elastic thread assembly within a passage formed between the first web layer and the second web layer, the passage defined between facing edges of pairs of adjacent bonds in the plurality of bond lines;

feeding the plurality of unbonded multifilament elastic threads under tension in a machine direction toward an ultrasonic bonding assembly; and combining together a subset of the plurality of unbonded multifilament elastic threads upstream of the ultrasonic bonding assembly so that the elastic thread assembly is now combined, wherein the facing edges are spaced apart by a distance that is smaller than an overall diameter of the elastic thread assembly in a non-tensioned state and that is larger than a strand diameter of the plurality of elastic threads in a non-tensioned state.

2. The method of claim 1 further comprising:

positioning a second elastic thread assembly between the first web layer and the second web layer, wherein the second elastic thread assembly comprises a plurality of elastic threads; and anchoring each of the elastic thread assemblies within a respective passage formed between the first web layer and the second web layer; each respective passage defined between facing edges of pairs of adjacent bonds in the plurality of bond lines.

3. The method of claim 1 further comprising ultrasonically bonding the first web layer to the second web layer to form the bond pattern.

4. The method of claim 1 further comprising forming the bond pattern using a rotary anvil having a face with a plurality of welding lines defined thereon, each welding line of the plurality of welding lines comprising a plurality of evenly spaced projections.

5. The method of claim 1 further comprising feeding the elastic thread assembly under tension in a machine direction; and wherein anchoring the elastic thread assembly within the passage comprises anchoring the elastic thread assembly between facing edges of the pairs of adjacent bonds that are oriented non-parallel to the machine direction.

6. The method of claim 1 further comprising combining together the subset of the plurality of elastic threads within a feeder device of a creel.

7. The method of claim 1 further comprising combining together the subset of the plurality of elastic threads within a guide roller.

\* \* \* \* \*